United States Patent [19]
Stein et al.

[11] 4,031,545
[45] June 21, 1977

[54] RADIANT ENERGY ALARM SYSTEM

[75] Inventors: Jay A. Stein, Framingham; Martin Annis, Newton, both of Mass.

[73] Assignee: American Science & Engineering, Inc., Cambridge, Mass.

[22] Filed: Sept. 8, 1975

[21] Appl. No.: 611,230

[52] U.S. Cl. .............................. 358/108; 358/111; 250/263

[51] Int. Cl.² ......................................... H04N 7/18

[58] Field of Search ............... 178/DIG. 1, DIG. 5, 178/6.8; 250/363; 358/108, 111

[56] References Cited

UNITED STATES PATENTS

| | | | |
|---|---|---|---|
| 3,049,588 | 8/1962 | Barmett | 178/6 |
| 3,758,723 | 9/1973 | Green | 178/6.8 |
| 3,919,467 | 11/1975 | Peugeot | 178/6.8 |
| 3,924,064 | 12/1975 | Namura et al. | 178/6.8 |

*Primary Examiner*—Robert L. Richardson
*Assistant Examiner*—Edward L. Coles
*Attorney, Agent, or Firm*—Charles Hieken; Jerry Cohen

[57] ABSTRACT

An X-ray inspection system includes a circuit that responds to a high level of opacity for more than a predetermined time interval by providing an alarm signal to alert the inspector of the possibility of concealed contraband. The circuitry also provides a pulse when exceptional opacity is detected for combination with the vertical deflection signal to translate the display of exceptionally opaque objects to a different portion of the viewing screen to facilitate identification of potential contraband without opening the baggage or parcel being inspected.

8 Claims, 14 Drawing Figures

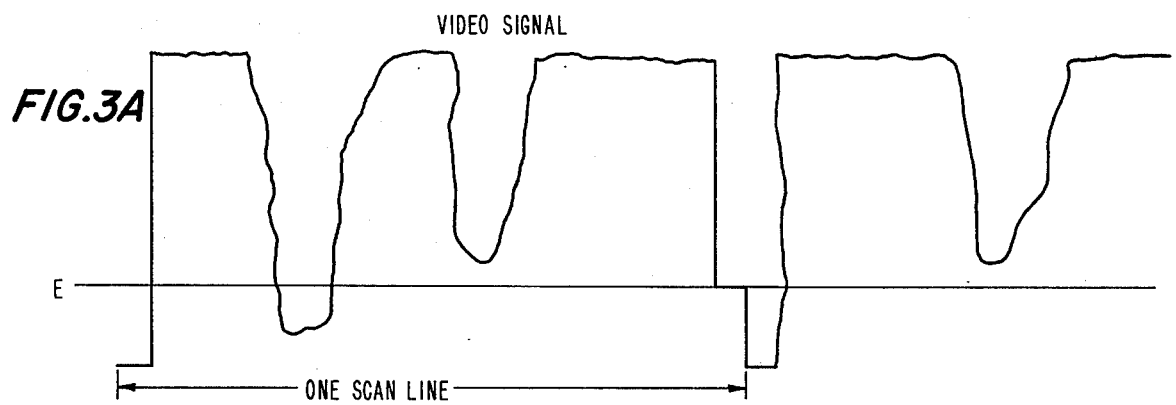
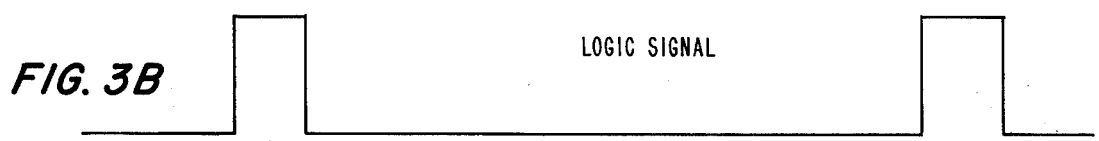
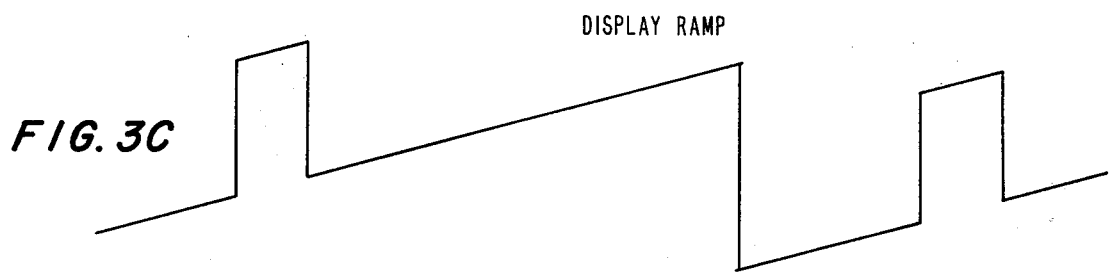
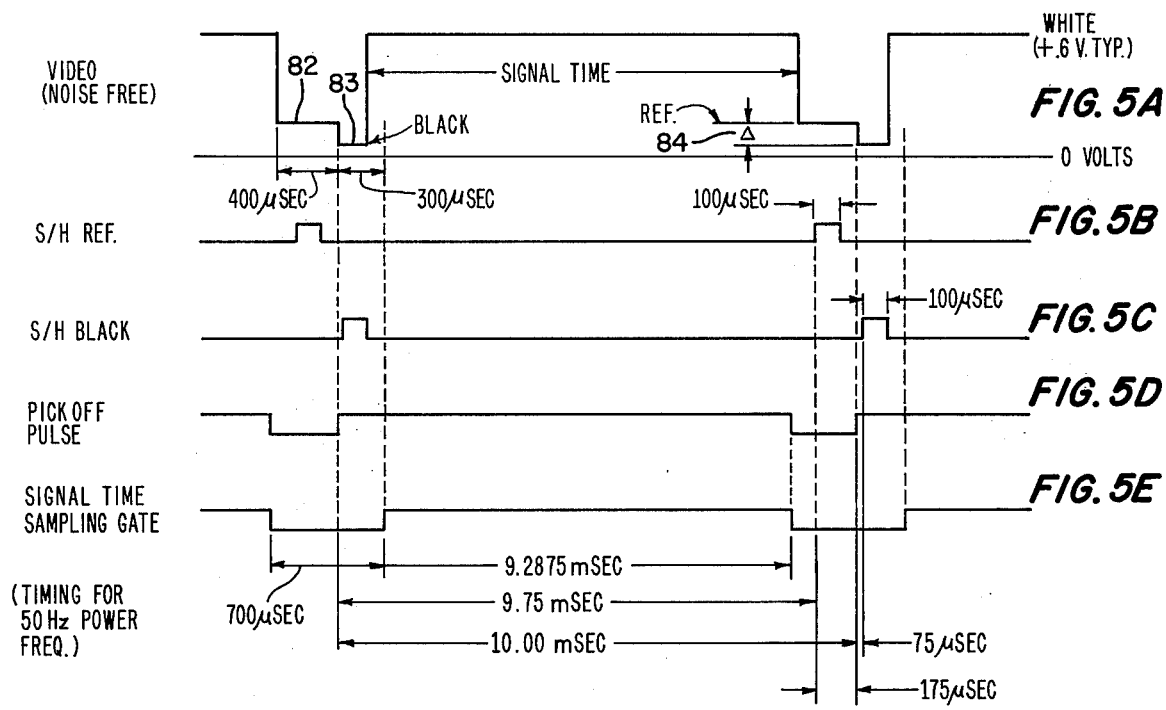

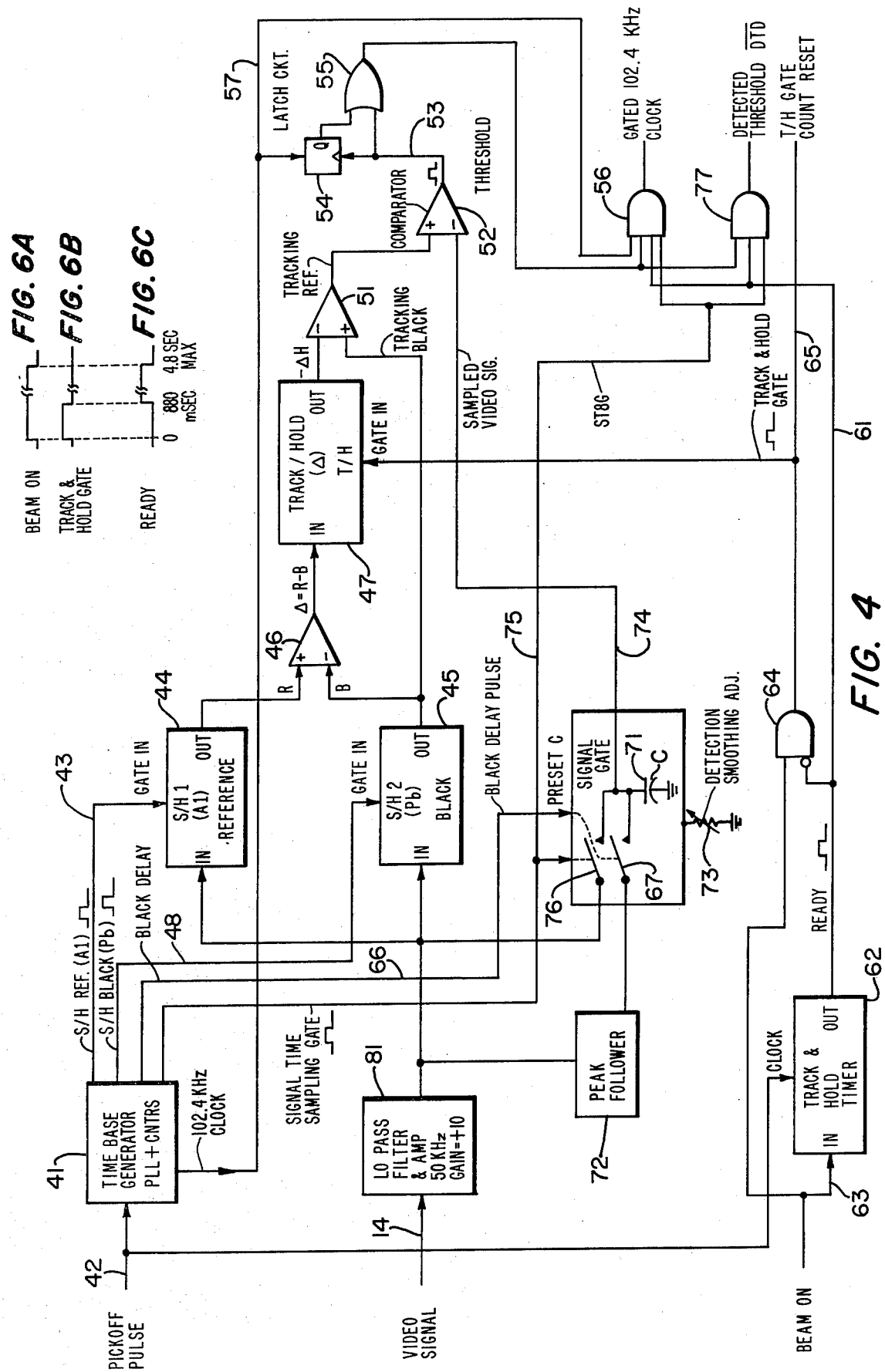

RADIANT ENERGY ALARM SYSTEM

BACKGROUND OF THE INVENTION

The present invention relates in general to alerting and more particularly concerns novel apparatus and techniques for use with an X-ray inspection system, such as the commercially available AS&E MICRO-DOSE system used for inspecting baggage and other parcels for contraband, that automatically provides an alarm signal upon sensing potential contraband while separately displaying the item that may be the contraband to facilitate a rapid determination of whether concealed contraband is in the bag or package. These results are achieved with apparatus that is relatively inexpensive, reliable and advantageously employs existing components of an X-ray imaging system.

The problem of detecting contraband concealed in packages and baggage is a serious one. The AS&E MICRO-DOSE X-ray inspection system has helped solve this problem for a number of leading airlines while inspecting carry-on baggage and parcels. That system includes means for scanning a line X-ray detector with a pencil beam of X-ray energy to provide a line image signal characteristic of the X-ray response of the parcel being scanned, and a television display system for displaying the sequence of image signals derived from the line detector as the parcel moves past. The detector comprises sodium iodide crystals that produce a visible manifestation of the intensity of the incident radiation that is sensed by a photodetector to provide a characteristic video output signal that may be applied to the television display having an image storage tube. The television picture tube displays an image of the contents of the parcels being scanned so that the operator may identify objects that may be contraband, such as a gun, bomb or knife. This system has such a high resolution that it is possible in most cases to readily distinguish between the presence and absence of contraband. However, the operator must make a judgment based on observing the picture as to whether a particular parcel should be opened and manually examined. Should the operator fail to make a proper judgment, it is possible that a parcel containing contraband might not be detected.

Accordingly, it is an important object of the invention to provide apparatus and techniques for automatically alerting inspection personnel of the possibility of contraband in a parcel being inspected.

It is a further object of the invention to achieve the preceding object with apparatus that is reliable, relatively inexpensive and advantageously employs existing components of an X-ray inspection system.

It is a further object of the invention to achieve one or more of the preceding objects while presenting a separate display of an item that may be contraband to facilitate identification of contraband without opening the parcel where practical.

It is a further object of the invention to achieve one or more of the preceding objects by sensing objects having an X-ray opacity greater than a predetermined level.

SUMMARY OF THE INVENTION

According to the invention, there is means including a radiation detector for scanning an item to be detected with radiant energy to provide a video signal representative of the opacity of the item being scanned to the radiant energy and means responsive to the video signal for indicating an alarm condition when the opacity characterized by the video signal is greater than a predetermined level for a predetermined time interval. In a more specific form of the invention, when the video signal exceeds a predetermined threshold level, gating means pass clock pulses to counting means to accumulate a count representative of the time the video signal remains beyond the threshold level. If the count exceeds a predetermined count, alarm means provides an alarm indication. According to another feature of the invention, an offsetting signal is provided when the video signal is beyond the threshold level that is coupled to the vertical deflection signal of the television display to produce a step in the vertical deflection signal that effectively displaces the picture being displayed so that the image of objects with opacity beyond the threshold level are displayed separately from the rest of the image. According to another feature of the invention, the detector includes means, such as one or both of a lead or aluminum plate, for establishing at least one reference level of known opacity.

Numerous other features, objects and advantages of the invention will become apparent from the following specification when read in connection with the accompanying drawing in which:

BRIEF DESCRIPTION OF THE DRAWING

FIGS. 3A-3C are graphical representations of signal waveforms plotted to a common time scale helpful in understanding the principles of the invention;

FIG. 4 is a detailed block diagram of elements in an exemplary system according to the invention; and FIGS. 5 and 6 are graphical representations of pertinent signal waveforms plotted to respective common time scales helpful in understanding the operation of the system of FIG. 4.

DETAILED DESCRIPTION OF THE PREFERRED EMBODIMENTS

Figure 1:
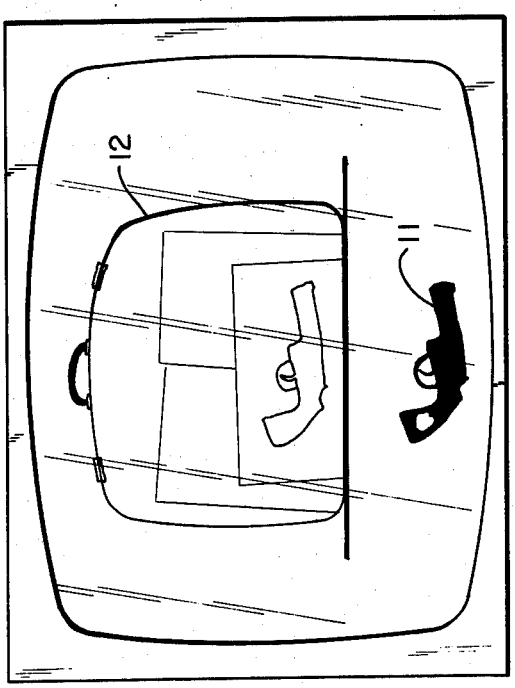
FIG. 1 is a front view of a television display according to the invention in which the image of a concealed weapon is shown displaced from the image of the bag in which it is concealed.

With reference now to the drawing and more particularly FIG. 1 thereof, there is shown a television display of the image of a concealed pistol 11 displaced below the image 12 of a suitcase in which it is concealed according to the invention so that when the alarm signal occurs, the operator may immediately examine the screen and determine that the suitcase should be manually inspected and searched for the pistol.

Figure 2:
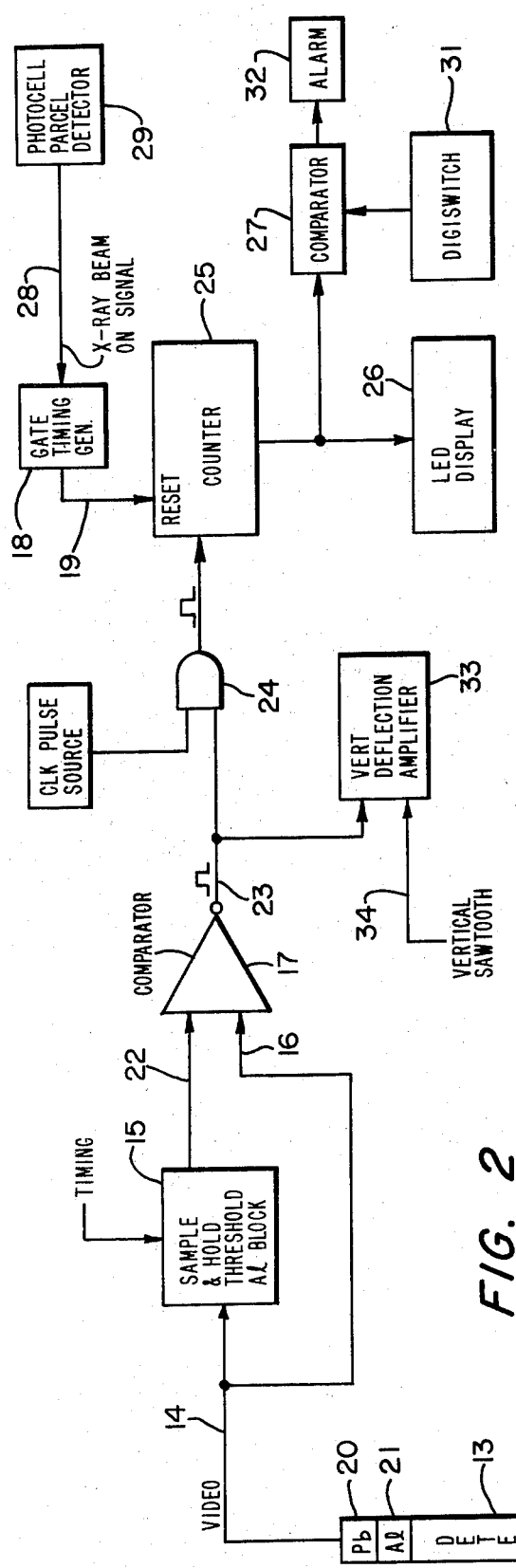
FIG. 2 is a block diagram illustrating the logical arrangement of a system according to the invention.

Referring to FIG. 2, there is shown a block diagram illustrating the logical arrangement of a system according to the invention showing just enough of the elements of an existing X-ray inspection system as will suffice to show the connection of the invention therewith. The prior art system includes a line detector 13 that is normally vertical and scanned from top to bottom by a pencil beam of X-rays while a conveyor belt carries a parcel to be inspected across the detector. The detector 13 includes a photomultiplier tube (PMT) (not shown) that provides a video signal representative of the opacity to X-rays of the object being scanned. The detector typically comprises a line of scintillation material such as sodium iodide which provide light of intensity that is proportional to the incident X-ray intensity. A PMT or other photoelectric transducer converts this light intensity into a corresponding electrical signal that is the video signal on line 14 that is applied to the sample and hold threshold circuit 15 and to input 16 of comparator 17. Typically detector 13 is 28 inches high by 1.25 inches wide and, according to the invention, is covered with an aluminum plate 21 and lead plate 20 at the top, typically 1.5 inches square and 1.0 inch thick and above the normal height of objects being scanned so that the first signals produced on line 14 are representative of the opacity of aluminum plate 21 and lead plate 20. Signal representing opacity of lead plate 20 is used to establish zero level in order to compensate for possible long light decay effects or afterflow in NaI crystal although circuitry for this is not shown in FIG. 2 in order to simplify this figure. The signal from the aluminum plate is held by sample and hold threshold circuit 15 and applied to the input 22 of comparator 17 so that comparator 17 provides an output signal on output line 23 only when the video signal level on line is less than the reference level on line 22.

The output of comparator 17 provides a gating signal to AND gate 24 to enable the latter to pass clock pulses to counter 25 after being reset by the track and hold gate pulse provided by the gate timing generator 18 on line 19. The gate timing generator 18 receives an X-ray beam on signal on line 28 from the photocell parcel detector 29 which detects the entrance of a new parcel into the scanning beam and which also turns on the X-rays. The count in counter 25 is displayed on display 26 and compared by comparator 27 with a preselected count set by digiswitch 31 to provide an alarm condition when the count in counter 25 exceeds that set in digiswitch 31. Typically alarm 32 may be audible, visible, tactile or combinations thereof, or the alarm signal may be used, for example, to stop the conveyor and require manual inspection of the parcel just inspected.

The output of comparator 17 on line 23 may also be applied to vertical ramp generator 33 that provides vertical deflection signals for the television display for combination with the vertical sawtooth signal on line 34 to produce a pedestal that displaces the vertical position of the image of the dense object from the image of the parcel in which it is concealed.

Referring to FIGS. 3A–3C, there are shown signal waveforms plotted to a common time scale helpful in understanding the mode of operation of the invention. FIG. 3A shows a typical video signal provided on line 14 and defines a threshold having a level E established when the beam scans the aluminum plate 21. When the video signal level is less than the threshold level, comparator 17 provides a logic signal as represented in FIG. 3B. This logic signal is superimposed upon the vertical sawtooth in vertical deflection amplifier 33 as indicated in FIG. 3C to produce the displaced display shown in FIG. 1.

Referring to FIG. 4, there is shown a more detailed block diagram of an embodiment according to the invention. The system according to the invention comprises a time base generator 41 that responds to a pickoff pulse applied on line 42 representative of the start of a scan; that is, when the pencil beam commences a top-to-bottom scan of detector 13. Time base generator 41 then provides signals on lines 43 and 48 representative of the times that the pencil beam is scanning the aluminum and lead squares 21 and 20, respectively, to gate the aluminum sample and hold circuit 44 and the lead or black sample and hold circuit 45 to provide reference and black levels, respectively, that are applied to + and − inputs, respectively, of diffference amplifier 46 to provide a difference signal that is applied to track and hold circuit 47. Circuit 47 averages and inverts this difference signal and applies it to the negative input of difference amplifier 51. The + input of difference amplifier 51 receives the black level output provided by black level source 45 to provide a tracking reference signal on the + input of comparator 52 which is the sum of the black level and the averaged difference level. Comparator 52 also receives a sampled video signal on its − input to provide an output signal on line 53 when the sampled video signal is less than the tracking reference level on the + input to enable latch circuit 54 and OR gate 55 to provide a signal that enables output gate 56 to transmit the 102.4 kHz clock pulses on line 57 provided by time base generator 41 when enabled. Output gate 56 is enabled by the ready potential on line 61 provided by track and hold timer 62 which delays by 740 milliseconds the beam on signal at input 63 derived from the X-ray scanning system indicating that the pencil beam is on. Pickoff pulses on line 42 clock the circuit so that counting is based upon pickoff pulses which occur during the period of time after the pencil beam has intercepted the parcel being scanned by the pencil beam. The ready signal on line 61 is also coupled to the NOT input of AND gate 64 which also receives the beam-on signal on line 63 to provide a track and hold gate pulse on line 65 that resets counter 25 to zero and enables track and hold circuit 47 during the interval when the pencil beam scans the aluminum and lead plates on detector 13.

Time base generator 41 also provides a black delay pulse on line 66 that closes switch 67 in response to a black delay pulse that occurs to preset the potential on capacitor 71 at a white level of the video signal provided by peak follower 72. Potentiometer 73 is in series with capacitor 71 to adjust the time constant of circuitry comprising capacitor 71 so that the potential on line 74 is related to the average of the sampled video signal.

Time base generator 41 also provides a signal time sampling gate signal on line 75 that closes switch 76 and enables output gate 56 and detected threshold gate 77. The video signal on line 14 is coupled to low pass filter amplifier 81 having a band pass typically to 50kHz and a gain of 10 for providing a smooth sampled video signal that line 74 carries to the − input of comparator 52 through closed switch 76.

Referring to FIGS. 5A–E, there is shown a graphical representation of pertinent signal waveforms helpful in understanding the operation of the system. FIG. 5A is a graphical representation of the video signals showing the video signals 82 and 83 provided when scanning the aluminum and lead blocks 21 and 20, respectively, to provide reference and black levels, respectively, and showing the difference between these two levels 84 provided by track and hold circuit 47. FIG. 5B shows the sample and hold reference pulses provided on line 43, FIG. 5C shows the black pulse provided on line 44, FIG. 5D shows the pickoff pulse provided on line 42 derived from X-ray system timing and FIG. 5E shows the signal time sampling gate on line 75. The specific time dimensions are representative for a 50 Hz power frequency and are inversely proportional to different power frequencies.

FIGS. 6A–6C are graphical representations of other signal waveforms plotted to a common time scale helpful in understanding principles of the invention. FIG. 6A is the beam on signal present when the pencil beam is on and applied on line 63, FIG. 6B is the track and hold gate signal provided by AND gate 64 on line 65 and FIG. 6C is the ready signal provided by track and hold timer 62 on line 61.

A feature of the invention is the ability to detect potential contraband that might be obscured in an X-ray image of an item being scanned. For example, the invention may effectively be used to establish a window or combination of windows recognizing signals representative of contraband. The system described above, for example, may produce an alarm signal in which the window is exceeding a predetermined threshold level of opacity for at least a predetermined area of scan typically corresponding to a predetermined time duration. The invention may also be useful in detecting letter bombs by detecting coincidence of two characteristics of a letter occurring simultaneously. The first is the existence of a large area of fairly thick material typically characteristic of the plastic explosive as one window. The second is the existence of a small thick piece of material typically characteristic of a metal containing the detonator as the second window. From the foregoing discussion and applying principles known to those having ordinary skill in the art, logical circuitry may readily be assembled for producing an alarm on the occurrence of these conditions.

There has been described apparatus and techniques for automatically alerting inspection personnel to the presence of potentially concealed contraband in parcels being inspected. The apparatus may be readily retrofitted to existing commercially available AS&E MICRO-DOSE X-ray inspection systems. The apparatus is relatively compact and inexpensive, relatively easy to manufacture and operates with great reliability. The separate display of the image of the object causing the alarm signal facilitates rapid visual inspection without opening the parcel to make an initial determination as to whether the likelihood of the object being contraband is sufficiently great to justify manual inspection of the parcel.

It is evident that those skilled in the art may now make numerous uses and modification of and departures from the specific embodiments described herein without departing from the principles of the invention. Consequently, the invention is to be construed as embracing each and every novel feature and novel combination of features present in or possessed by the apparatus and techniques herein disclosed.

What is claimed is:

1. In a radiant energy imaging system having a scanning beam of radiant energy that scans a radiant energy detector to provide video signals representative of the opacity of objects intercepting the radiant energy beam alerting apparatus comprising,
 a source of a signal of reference level corresponding to a predetermined reference opacity,
 means for comparing said video signal with said reference signal to provide a threshold signal when the video signal bears a predetermined relationship to the reference signal,
 means for indicating an alarm condition when said threshold signal occurs for a predetermined time interval,
 wherein said source of a reference signal comprises a predetermined portion of said video signal produced when said beam is scanning a predetermined reference object of known opacity between said detector and the source of said radiant energy beam.

2. In a radiant energy imaging system having a scanning beam of radiant energy that scans a radiant energy detector to provide video signals representative of the opacity of objects intercepting the radiant energy beam alerting apparatus comprising,
 a source of a signal of reference level corresponding to a predetermined reference opacity,
 means for comparing said video signal with said reference signal to provide a threshold signal when the video signal bears a predetermined relationship to the reference signal,
 means for indicating an alarm condition when said threshold signal occurs for a predetermined time interval,
 and means responsive to said threshold signal for altering a deflection signal in the television display of the image of the object being scanned to displace the image of potential contraband from the image of the rest of the object being scanned.

3. In a radiant energy imaging system having a scanning beam of radiant energy that scans a radiant energy detector to provide video signals representative of the opacity of objects intercepting the radiant energy beam alerting apparatus comprising,
 a source of a signal of reference level corresponding to a predetermined reference opacity,
 means for comparing said video signal with said reference signal to provide a threshold signal when the video signal bears a predetermined relationship to the reference signal,
 means for indicating an alarm condition when said threshold signal occurs for a predetermined time interval,
 a source of clock pulses,
 a counter,
 gating means responsive to said threshold signal for transmitting clock pulses from said clock pulse source to said counter upon occurrence of said threshold signal,
 said means for indicating an alarm condition including means responsive to the count in said counter for producing said alarm condition when the count in said counter exceeds a predetermined number.

4. In a radiant energy imaging system having a scanning beam of radiant energy that scans a radiant energy detector to provide video signals representative of the opacity of objects intercepting the radiant energy beam alerting apparatus comprising,
 a source of a signal of reference level corresponding to a predetermined reference opacity,
 means for comparing said video signal with said reference signal to provide a threshold signal when the video signal bears a predetermined relationship to the reference signal,
 means for indicating an alarm condition when said threshold signal occurs for a predetermined time interval,
 and a sample of material of known opacity adjacent to said radiant energy detector for intercepting said beam of radiant energy during a portion of the scan thereof so that the video signal then provided by said radiant energy detector comprises said source of a signal of reference level.

5. Alerting apparatus in accordance with claim 4 and further comprising a second element of known opacity adjacent to said radiant energy detector for intercepting said scanning beam so that said radiant energy detector then provides a video signal representing that known opacity and comprises a source of a signal of a second level corresponding to a predetermined second reference opacity.

6. Alerting apparatus in accordance with claim 4 wherein said item of known opacity is made of aluminum.

7. Alerting apparatus in accordance with claim 5 wherein one of said items of known opacity is made of aluminum and the other is made of lead.

8. A method of using alerting apparatus in a radiant energy imaging system having a scanning beam of radiant energy that scans a radiant energy detector to provide video signals representative of the opacity of objects intercepting the radiant energy beam comprising, a source of a signal of reference level corresponding to a predetermined reference opacity, means for comparing said video signal with said reference signal to provide a threshold signal when the video signal bears a predetermined relationship to the reference signal, means for indicating an alarm condition when said threshold signal occurs for a predetermined time interval, which method includes the steps of establishing a signal representing a first window of potential contraband designating a first combination of opacity and area representing potential contraband, establishing a second window corresponding to a predetermined combination of opacity and area ranges characteristic of a particular type of contraband upon the occurrence of a video signal within said first window, and indicating an alarm condition upon the occurrence of scanning an item causing the production of video signals within both said first and second windows.

* * * * *